(12) United States Patent
Szpak et al.

(10) Patent No.: US 10,123,770 B2
(45) Date of Patent: Nov. 13, 2018

(54) PATIENT SUPPORT SYSTEM

(71) Applicant: Delphinus Medical Technologies, Inc., Plymouth, MI (US)

(72) Inventors: James Szpak, Plymouth, MI (US); Nebjosa Duric, Plymouth, MI (US); Peter Littrup, Plymouth, MI (US); Roman Janeer, Plymouth, MI (US); Mike Tesic, Plymouth, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 69 days.

(21) Appl. No.: 14/208,181

(22) Filed: Mar. 13, 2014

(65) Prior Publication Data

US 2014/0276068 A1    Sep. 18, 2014

Related U.S. Application Data

(60) Provisional application No. 61/778,985, filed on Mar. 13, 2013.

(51) Int. Cl.
*A61B 8/00* (2006.01)
*A61B 8/08* (2006.01)
*A61B 8/14* (2006.01)

(52) U.S. Cl.
CPC .......... *A61B 8/406* (2013.01); *A61B 8/0825* (2013.01); *A61B 8/145* (2013.01); *A61B 8/42* (2013.01); *A61B 8/4494* (2013.01)

(58) Field of Classification Search
CPC ....... A61B 8/0825; A61B 8/145; A61B 8/406; A61B 8/42; A61B 8/4494
See application file for complete search history.

(56) References Cited

U.S. PATENT DOCUMENTS

| 3,154,067 A | 10/1964 | Stenstrom et al. |
| 3,771,355 A | 11/1973 | Sachs |

(Continued)

FOREIGN PATENT DOCUMENTS

| AU | 3443295 A | 5/1996 |
| CA | 2324602 A | 9/1999 |

(Continued)

OTHER PUBLICATIONS

Chan et al., An Agglomeration Multigrid Method for Unstructured Grids, Contemporary Mathematics, vol. 218, 1998.

(Continued)

*Primary Examiner* — Michael Rozanski
(74) *Attorney, Agent, or Firm* — Wilson Sonsini Goodrich & Rosati

(57) ABSTRACT

A system for supporting a patient while scanning a volume of tissue protruding from a patient includes a base having a planar portion configured to support the patient in a prone configuration. A frustoconical portion extends from the planar portion and defines a base aperture configured to receive the volume of tissue. A support assembly couples to the base. A membrane is retained in tension within a frame at a peripheral portion of the membrane. The membrane defines a membrane aperture configured to align with the base aperture, and the membrane is configured to deflect into the frustoconical portion of the base in response to the patient's weight. The system can further include an electrical subsystem including a pressure sensor array configured to generate signals in response to a pressure distribution resulting from the patient's weight at the patient interface system.

22 Claims, 5 Drawing Sheets

(56) References Cited

U.S. PATENT DOCUMENTS

| | | | |
|---|---|---|---|
| 3,881,466 A | 5/1975 | Wilcox | |
| 3,886,489 A | 5/1975 | Jones | |
| 3,925,610 A | 12/1975 | French et al. | |
| 4,015,836 A * | 4/1977 | Redington | A61B 6/04 |
| | | | 5/601 |
| 4,028,934 A | 6/1977 | Sollish | |
| 4,059,010 A | 11/1977 | Sachs | |
| 4,075,883 A | 2/1978 | Glover | |
| 4,105,018 A | 8/1978 | Greenleaf et al. | |
| 4,144,877 A | 3/1979 | Frei et al. | |
| 4,222,274 A | 9/1980 | Johnson | |
| 4,250,894 A | 2/1981 | Frei et al. | |
| 4,317,369 A | 3/1982 | Johnson | |
| 4,328,707 A | 5/1982 | Clement et al. | |
| 4,363,326 A | 12/1982 | Kopel | |
| 4,412,288 A | 10/1983 | Herman | |
| 4,431,008 A | 2/1984 | Wanner et al. | |
| 4,433,690 A | 2/1984 | Green et al. | |
| 4,481,948 A | 11/1984 | Sole | |
| 4,509,368 A | 4/1985 | Whiting et al. | |
| 4,515,165 A | 5/1985 | Carroll | |
| 4,541,436 A | 9/1985 | Hassler et al. | |
| 4,542,744 A | 9/1985 | Barnes et al. | |
| 4,562,540 A | 12/1985 | Devaney | |
| 4,564,019 A | 1/1986 | Miwa | |
| 4,606,342 A | 8/1986 | Zamba et al. | |
| 4,646,756 A | 3/1987 | Watmough et al. | |
| 4,662,222 A | 5/1987 | Johnson | |
| 4,671,256 A | 6/1987 | Lemelson | |
| 4,722,056 A | 1/1988 | Roberts et al. | |
| 4,733,562 A | 3/1988 | Saugeon | |
| 4,855,911 A | 8/1989 | Lele et al. | |
| 4,858,124 A | 8/1989 | Lizzi et al. | |
| 4,917,096 A | 4/1990 | Englehart et al. | |
| 4,932,414 A | 6/1990 | Coleman et al. | |
| 4,941,474 A | 7/1990 | Pratt, Jr. | |
| 5,003,979 A | 4/1991 | Merickel et al. | |
| 5,025,792 A | 6/1991 | Hon et al. | |
| 5,029,476 A | 7/1991 | Metala et al. | |
| RE33,672 E | 8/1991 | Miwa | |
| 5,095,909 A | 3/1992 | Nakayama et al. | |
| 5,103,129 A | 4/1992 | Slayton et al. | |
| 5,143,069 A | 9/1992 | Kwon et al. | |
| 5,158,071 A | 10/1992 | Umemura et al. | |
| 5,158,536 A | 10/1992 | Sekins et al. | |
| 5,178,147 A | 1/1993 | Ophir et al. | |
| 5,179,455 A | 1/1993 | Garlick | |
| 5,212,571 A | 5/1993 | Garlick et al. | |
| 5,255,683 A | 10/1993 | Monaghan | |
| 5,260,871 A | 11/1993 | Goldberg | |
| 5,267,566 A | 12/1993 | Choucair et al. | |
| 5,268,876 A | 12/1993 | Rachlin | |
| 5,269,309 A | 12/1993 | Fort et al. | |
| 5,280,788 A | 1/1994 | Janes et al. | |
| 5,289,520 A * | 2/1994 | Pellegrino | A61B 6/0435 |
| | | | 600/461 |
| 5,296,910 A | 3/1994 | Cole | |
| 5,297,553 A | 3/1994 | Sliwa et al. | |
| 5,304,173 A | 4/1994 | Kittrell et al. | |
| 5,305,752 A | 4/1994 | Spivey et al. | |
| 5,318,028 A | 6/1994 | Mitchell et al. | |
| 5,329,817 A | 7/1994 | Garlick et al. | |
| 5,339,282 A | 8/1994 | Kuhn et al. | |
| 5,349,954 A | 9/1994 | Tiemann et al. | |
| 5,372,138 A | 12/1994 | Crowley et al. | |
| 5,394,875 A | 3/1995 | Lewis et al. | |
| 5,398,691 A | 3/1995 | Martin et al. | |
| 5,413,108 A | 5/1995 | Alfano | |
| 5,415,164 A | 5/1995 | Faupel et al. | |
| 5,421,338 A | 6/1995 | Crowley et al. | |
| 5,433,202 A | 7/1995 | Mitchell et al. | |
| 5,463,548 A | 10/1995 | Asada et al. | |
| 5,465,722 A | 11/1995 | Fort et al. | |
| 5,474,072 A | 12/1995 | Shmulewitz | |
| 5,479,927 A | 1/1996 | Shmulewitz | |
| 5,485,839 A | 1/1996 | Aida et al. | |
| 5,487,387 A | 1/1996 | Trahey et al. | |
| 5,492,126 A | 2/1996 | Hennige et al. | |
| 5,501,655 A | 3/1996 | Rolt et al. | |
| 5,513,639 A | 5/1996 | Satomi et al. | |
| 5,524,630 A | 6/1996 | Crowley | |
| 5,546,945 A | 8/1996 | Soldner | |
| 5,548,658 A | 8/1996 | Ring et al. | |
| 5,553,618 A | 9/1996 | Suzuki et al. | |
| 5,558,092 A | 9/1996 | Unger et al. | |
| 5,573,497 A | 11/1996 | Chapelon | |
| 5,582,173 A | 12/1996 | Li | |
| 5,588,032 A | 12/1996 | Johnson et al. | |
| 5,588,430 A | 12/1996 | Bova et al. | |
| 5,590,653 A | 1/1997 | Aida et al. | |
| 5,590,657 A | 1/1997 | Cain et al. | |
| 5,596,992 A | 1/1997 | Haaland et al. | |
| 5,606,971 A | 3/1997 | Sarvazyan | |
| 5,609,152 A | 3/1997 | Pellegrino et al. | |
| 5,620,479 A | 4/1997 | Diederich | |
| 5,640,956 A | 6/1997 | Getzinger et al. | |
| 5,643,179 A | 7/1997 | Fujimoto | |
| 5,660,185 A | 8/1997 | Shmulewitz et al. | |
| 5,664,573 A | 9/1997 | Shmulewitz | |
| 5,673,698 A | 10/1997 | Okada et al. | |
| 5,678,565 A | 10/1997 | Sarvazyan | |
| 5,715,825 A | 2/1998 | Crowley | |
| 5,722,411 A | 3/1998 | Suzuki et al. | |
| 5,743,863 A | 4/1998 | Chapelon | |
| 5,749,364 A | 5/1998 | Sliwa, Jr. et al. | |
| 5,759,162 A | 6/1998 | Oppelt et al. | |
| 5,762,066 A | 6/1998 | Law et al. | |
| 5,766,129 A | 6/1998 | Mochizuki | |
| 5,785,663 A | 7/1998 | Sarvazyan | |
| 5,787,049 A | 7/1998 | Bates | |
| 5,797,849 A | 8/1998 | Vesely et al. | |
| 5,800,350 A | 9/1998 | Coppleson et al. | |
| 5,810,731 A | 9/1998 | Sarvazyan et al. | |
| 5,817,025 A | 10/1998 | Alekseev et al. | |
| 5,830,133 A | 11/1998 | Osten et al. | |
| 5,833,614 A | 11/1998 | Dodd et al. | |
| 5,833,627 A | 11/1998 | Shmulewitz et al. | |
| 5,833,633 A | 11/1998 | Sarvazyan | |
| 5,833,634 A | 11/1998 | Laird et al. | |
| 5,836,882 A | 11/1998 | Frazin | |
| 5,836,894 A | 11/1998 | Sarvazyan | |
| 5,846,202 A | 12/1998 | Ramamurthy et al. | |
| 5,851,182 A | 12/1998 | Sahadevan | |
| 5,855,554 A | 1/1999 | Schneider et al. | |
| 5,865,167 A | 2/1999 | Godik | |
| 5,865,743 A | 2/1999 | Godik | |
| 5,891,619 A | 4/1999 | Zakim et al. | |
| 5,945,674 A | 8/1999 | Dukor | |
| 6,002,958 A | 12/1999 | Godik | |
| 6,005,916 A | 12/1999 | Johnson et al. | |
| 6,014,473 A | 1/2000 | Hossack et al. | |
| 6,023,632 A | 2/2000 | Wilk | |
| 6,050,943 A | 4/2000 | Slayton et al. | |
| 6,056,690 A | 5/2000 | Roberts | |
| 6,078,677 A | 6/2000 | Dolleman et al. | |
| 6,083,166 A | 7/2000 | Holdaway et al. | |
| 6,102,857 A | 8/2000 | Kruger | |
| 6,109,270 A | 8/2000 | Mah et al. | |
| 6,117,080 A | 9/2000 | Schwartz | |
| 6,135,960 A | 10/2000 | Holmberg | |
| 6,146,897 A | 11/2000 | Cohenford et al. | |
| 6,149,441 A | 11/2000 | Pellegrino et al. | |
| 6,165,734 A | 12/2000 | Garini et al. | |
| 6,190,334 B1 | 2/2001 | Lasky et al. | |
| 6,235,038 B1 | 5/2001 | Hunter et al. | |
| 6,242,472 B1 | 6/2001 | Sekins et al. | |
| 6,245,017 B1 | 6/2001 | Hashimoto et al. | |
| 6,256,090 B1 * | 7/2001 | Chen | G01V 1/3835 |
| | | | 250/227.14 |
| 6,289,235 B1 | 9/2001 | Webber et al. | |
| 6,292,682 B1 | 9/2001 | Kruger | |
| 6,296,489 B1 | 10/2001 | Blass et al. | |
| 6,317,617 B1 | 11/2001 | Gilhuijs et al. | |
| 6,351,660 B1 | 2/2002 | Burke et al. | |

(56) References Cited

U.S. PATENT DOCUMENTS

| | | | |
|---|---|---|---|
| 6,368,275 B1 | 4/2002 | Sliwa et al. | |
| 6,385,474 B1 | 5/2002 | Rather et al. | |
| 6,413,219 B1 | 7/2002 | Avila et al. | |
| 6,425,869 B1 | 7/2002 | Rafter et al. | |
| 6,428,477 B1 | 8/2002 | Mason | |
| 6,450,960 B1 | 9/2002 | Rather et al. | |
| 6,451,013 B1 | 9/2002 | Bays et al. | |
| 6,475,150 B2 | 11/2002 | Haddad | |
| 6,478,739 B1 | 11/2002 | Hong | |
| 6,490,469 B2 | 12/2002 | Candy | |
| 6,511,427 B1 | 1/2003 | Sliwa, Jr. et al. | |
| 6,527,759 B1 | 3/2003 | Tachibana et al. | |
| 6,540,678 B2 | 4/2003 | Rather et al. | |
| 6,559,178 B1 | 5/2003 | Zamoyski | |
| 6,574,499 B1 | 6/2003 | Dines et al. | |
| 6,587,540 B1 | 7/2003 | Johnson et al. | |
| 6,612,988 B2 | 9/2003 | Maor et al. | |
| 6,636,584 B2 | 10/2003 | Johnson et al. | |
| 6,645,202 B1 | 11/2003 | Pless et al. | |
| 6,672,165 B2 | 1/2004 | Rather et al. | |
| 6,716,412 B2 | 4/2004 | Unger | |
| 6,728,567 B2 | 4/2004 | Rather et al. | |
| 6,776,760 B2 | 8/2004 | Marmarelis | |
| 6,785,570 B2 | 8/2004 | Nir | |
| 6,810,278 B2 | 10/2004 | Webber et al. | |
| 6,837,854 B2 | 1/2005 | Moore et al. | |
| 6,883,194 B2 | 4/2005 | Corbeil et al. | |
| 6,926,672 B2 | 8/2005 | Moore et al. | |
| 6,939,301 B2 | 9/2005 | Abdelhak | |
| 6,984,210 B2 | 1/2006 | Chambers et al. | |
| 7,025,725 B2 | 4/2006 | Dione et al. | |
| 7,179,449 B2 | 2/2007 | Lanza et al. | |
| 7,285,092 B2 | 10/2007 | Duric et al. | |
| 7,346,203 B2 | 3/2008 | Turek et al. | |
| 7,497,830 B2 | 3/2009 | Li | |
| 7,530,951 B2 | 5/2009 | Fehre et al. | |
| 7,556,602 B2 | 7/2009 | Wang et al. | |
| 7,570,742 B2 | 8/2009 | Johnson et al. | |
| 7,742,796 B2* | 6/2010 | Eberhard | A61B 6/502 600/437 |
| 8,272,088 B2* | 9/2012 | Sliski | A61B 5/415 378/209 |
| 9,649,068 B2* | 5/2017 | DeFreitas | A61B 6/0435 |
| 2001/0029334 A1 | 10/2001 | Graumann et al. | |
| 2001/0037075 A1 | 11/2001 | Candy | |
| 2001/0051774 A1 | 12/2001 | Littrup et al. | |
| 2002/0065466 A1 | 5/2002 | Rather et al. | |
| 2002/0099290 A1 | 7/2002 | Haddad | |
| 2002/0120196 A1 | 8/2002 | Dubberstein et al. | |
| 2002/0131551 A1 | 9/2002 | Johnson et al. | |
| 2003/0138053 A1 | 7/2003 | Candy et al. | |
| 2004/0030227 A1 | 2/2004 | Littrup et al. | |
| 2004/0059265 A1 | 3/2004 | Candy et al. | |
| 2004/0081273 A1* | 4/2004 | Ning | A61B 6/032 378/37 |
| 2004/0122325 A1 | 6/2004 | Chambers et al. | |
| 2004/0152986 A1 | 8/2004 | Fidel et al. | |
| 2004/0167396 A1 | 8/2004 | Chambers et al. | |
| 2004/0181154 A1 | 9/2004 | Peterson et al. | |
| 2005/0165309 A1 | 7/2005 | Varghese et al. | |
| 2005/0196025 A1 | 9/2005 | Schofield | |
| 2005/0260745 A1 | 11/2005 | Domansky et al. | |
| 2006/0009693 A1 | 1/2006 | Hanover et al. | |
| 2006/0020205 A1 | 1/2006 | Kamiyama | |
| 2006/0064014 A1 | 3/2006 | Falco et al. | |
| 2006/0084859 A1 | 4/2006 | Johnson et al. | |
| 2006/0085049 A1 | 4/2006 | Cory et al. | |
| 2006/0287596 A1 | 12/2006 | Johnson et al. | |
| 2006/0293597 A1 | 12/2006 | Johnson et al. | |
| 2007/0015949 A1* | 1/2007 | Kaiser | A61F 13/02 600/1 |
| 2007/0167823 A1 | 7/2007 | Lee et al. | |
| 2007/0282200 A1 | 12/2007 | Johnson et al. | |
| 2008/0045864 A1 | 2/2008 | Candy et al. | |
| 2008/0058682 A1 | 3/2008 | Azhari et al. | |
| 2008/0218743 A1 | 9/2008 | Stetten et al. | |
| 2008/0229832 A1 | 9/2008 | Huang et al. | |
| 2008/0269812 A1 | 10/2008 | Gerber et al. | |
| 2008/0275344 A1 | 11/2008 | Glide-Hurst et al. | |
| 2008/0281205 A1 | 11/2008 | Naghavi et al. | |
| 2008/0294027 A1 | 11/2008 | Frinking et al. | |
| 2008/0294043 A1 | 11/2008 | Johnson et al. | |
| 2008/0319318 A1 | 12/2008 | Johnson et al. | |
| 2009/0035218 A1 | 2/2009 | Ross et al. | |
| 2009/0076379 A1 | 3/2009 | Hamill et al. | |
| 2009/0129556 A1* | 5/2009 | Ahn | A61B 6/04 378/208 |
| 2009/0143674 A1 | 6/2009 | Nields et al. | |
| 2010/0331699 A1 | 12/2010 | Yu et al. | |
| 2011/0152685 A1 | 6/2011 | Misono | |
| 2013/0267850 A1 | 10/2013 | Berman | |
| 2014/0316269 A1* | 10/2014 | Zhang | A61B 8/4494 600/439 |

FOREIGN PATENT DOCUMENTS

| | | |
|---|---|---|
| EP | 0097917 A | 1/1984 |
| EP | 284055 A | 9/1988 |
| EP | 317049 A | 5/1989 |
| EP | 320444 A | 6/1989 |
| EP | 351610 A | 1/1990 |
| EP | 538241 A | 4/1993 |
| EP | 0609922 A | 8/1994 |
| EP | 614651 A | 9/1994 |
| EP | 642762 A | 3/1995 |
| EP | 661029 A | 7/1995 |
| EP | 774276 A | 5/1997 |
| EP | 1063920 A | 1/2001 |
| GB | 2040642 A | 8/1980 |
| JP | 2005253827 A | 9/2005 |
| JP | 2007181679 A | 7/2007 |
| JP | 2009034521 A | 2/2009 |
| WO | 9947046 A | 9/1999 |
| WO | 199947046 | 9/1999 |
| WO | 0230288 A | 4/2002 |
| WO | 2002028350 | 4/2002 |
| WO | 2004061743 A | 7/2004 |
| WO | 2005057467 A | 6/2005 |
| WO | 2007023408 A | 3/2007 |

OTHER PUBLICATIONS

McCormick et al., Multigrid solution of a linearized, regularized least-squares problem in electrical impedance tomography, Inverse Problems 9, 1993, 697-713.

Oh et al., Multigrid Tomographic Inversion With Variable Resolution Data and Image Spaces, IEEE Transactions on Image Proessing, vol. 15, No. 9, Sep. 2006.

Quan et al., Sound-speed tomography using first-arrival transmission ultrasound for a ring array, Medical Imaging 2007: Ultrasonic Imaging and Signal Processing, Proc. of SPIE vol. 6513.

Zhang et al., A comparison of material classification techniques for ultrasound inverse imaging, J. Acoust. Soc. Am. 111 (1), Pt. 1, Jan. 2002.

Azhari et al., "Volumetric Imaging with Ultrasonic Spiral CT," Radiol 212 (1999) 270-275.

Banihashemi, B. et al., "Ultrasound Imaging of Apoptosis in Tumor Response: Novel Preclinical Monitoring of Photodynamic Therapy Effects." Cancer Research, vol. 68, No. 20, Oct. 15, 2008, pp. 8590-8596.

Barlow et al., "Prospective Breast Cancer Risk Prediction Model for Women Undergoing Screening Mammogrpahy," J. Nat'l Cancer Institute 98(17): 1204-1214 (2006).

Boone et al., "Dedicated Breast CT: Radiation Dose and Image Quality Evaluation," Med Phys 221(3): 657-667 (2001).

Boston et al., "Estimation of the Content of Fat and Parenchyma in Breast Tissue Using MRI T1 Histograms and Phantoms," MRI 23: 591-599 (2005).

Boyd, "Quantitative Classification of Mammographic Densities and Breast Cancer Risk: Results from the Canadian National Breast Screening Study," J Nat'l Cancer Institute 87(9): 670-675 (1995).

(56) References Cited

OTHER PUBLICATIONS

Byng et al., The Quantitative Analysis of Mammographic Densities,: Phys Med Biol 39 (1994) 1629-1638.
Cadzow, "Signal enhancement—A composite property mapping algorithm," IEEE Transactions on Acoustics, Speech and Signal Processing 36(1) (1988) 49-62.
Centerline, PortalVision section, Summer 2002 edition, published by Varian Medical Systems.
Chang et al., "Breast Density Analysis in 3-D Whole Breast Ultrasound Images," IEEE Proc 28th IEEE EMBS Annual International Conference (2006) 2795-2798.
Chang et al., Kirchhoff migration of ultrasonic images, Materials evaluation, V59, N3, 413-417, 2001.
Chelfouh et al., "Characterization of Urinary Calculi: in Vitro Study of 'Twinking Artifact' revealed by Color-Flow Sonography," AJR Am. J. Roentgenol. 171( 4) (1998) 1055-60.
Chen et al., "Projecting Absolute Invasive Breast Cancer Risk in White Women with a Model that Includes Mammographic Density," J. Nat'l Cancer Institute 98(17) (2006) 1215-1226.
Diederich et al., "The design of ultrasound applicators for interstitial hyperthermia," Ultrasonics Symposium, Proc IEEE 1993 Baltimore, MD, USA Oct. 31-Nov. 3, 1993, New York, NY, USA, 1215-1219.
Drineas et al., "Distance matrix reconstruction from incomplete distance information for sensor network localization," 3rd Annual IEEE Communications Society on Sensor and Ad Hoc Communications and Networks, Sep. 2006, pp. 536-544.
Duric et al. "Computed Ultrasound Risk Evaluation," Barbara Ann Karmanos Cancer Institute. pp. 1-23. 2008.
Duric et al., "Detection of Breast Cancer with Ultrasound Tomography: First Results with the Computed Ultrasound Risk Evaluation (CURE) Prototype," Med Phys 34(2) (2007).
Dussik, "The Ultrasonic Field as a Medical Tool," Amer J Phys Med 33(1) (1954) 5-20.
Fjield et al., "A Parametric Study of the Concentric-Ring Transducer Design for MRI Guided Ultrasound Surgery," J. Acoust. Soc. America 100 (2) Pt 1 (1996).
Gervias et al., "Renal Cell Carcinoma: Clinical Experience and Technical Success with Radio-frequency Ablation of 42 Tumors," Radiology 226 (2003) 417-424.
Glide et al., "Novel Approach to Evaluating Breast Density Utilizing Ultrasound Tomography," Med Phys 34(2) (2007) 744-753.
Glide, "A Novel Approach to Evaluating Breast Density Using Ultrasound Tomography," Dissertation Graduate School of Wayne State University (2007).
Glide-Hurst et al., "A Novel Ultrasonic Method for Measuring Breast Density and Breast Cancer Risk," Med Imaging 2008, Proc SPIE vol. 6920, 69200Q.
Glide-Hurst et al., "Volumetric breast density evaluation from ultrasound tomography images", Medical Physics, vol. 35, 2008, pp. 3988-3997.
Glide-Hurst, "A New Method for Quantitative Analysis of Mammographic Density," Med Phys 34(11) (2007) 4491-4498.
Greenleaf et al., "Artificial Cavitation Nuclei Significantly Enhance Acoustically Incuded Cell Transfection," Ultrasound Med & Biol 24 (1998) 587-595.
Greenleaf, "Computerized Tomography with Ultrasound," Proc IEEE 71(3) (1983) 330-337.
Hayashi, "A New Method of Measuring in Vivo Sound Speed in the Reflection Mode," J Clin Ultrasound 16(2) (1988) 87-93.
Jellins et al., "Velocity Compensation in Water-Coupled Breast Echography," Ultrasonics 11(5) (1973) 223-6.
Kaizer et al., "Ultrasonographically Defined Parenchymal Pattenrs of the Breast: Relationship to Mammographic Patterns and Other Risk Factors for Breast Cancer," Brit J Radiology 61(722) (1988) 118-24.
Karssemeijer, "Automated Classification of Parenchymal Patterns in Mammograms," Phys Med Biol 43 (1998) 365-378.

Kerlikowske et al., "Longitudinal Measurement of Clinical Mammographic Breast Density to Improve Estimation of Breast Cancer Risk," J. Nat'l Cancer Institute 99(5) (2007) 386-395.
Klimes, Grid Travel-time Tracing: Second-order Method for the First Arrivals in Smooth Media, PAGEOPH, vol. 148, Nos. 3/4, 1996.
Knapp et al., "The generalized correlation method for estimation of time delay," IEEE Transactions on Acoustics, Speech and Signal Processing 24(4) (1976) 320-327.
Kossoff et al., "Average Velocity of Ultrasound in the Human Female Breast," J Acoust Soc America 53(6) (1973) 1730-6.
Li et al., "Clinical Breast Imaging Using Sound-Speed Reconstructions of Ultrasound Tomography Data," Med Imaging 2008, Proc SPIE vol. 6920, 6920009.
Li et al., "In Vivo Breast Sound-Speed Imaging with Ultrasound Tomography", Ultrasound in Med & Bioi., vol. 35, No. 10, 2009, pp. 1615-1628.
Li et al., Breast Imaging Using Transmission Ultrasound: Reconstructing Tissue Parameters of Sound Speed and Attenuation,2008 International Conference on BioMedical Engineering and Informatics, IEEE computer society, 708-712.
Li et al., Refraction corrected transmission ultrasound computed tomography for application in breast imaging, Med. Phys. 37(5), May 2010, 2233-2246.
Louvar et al., "Correlation of Color Doppler Flow in the Prostate with Tissue Microvascularity," Cancer 1:83(1) (1998) 135-40.
Marias, "Automatic Labelling and BI-RADS Characterisation of Mammogram Densities," Proc 2005 IEEE, Sep. 1-4, 2005, pp. 6394-6398.
Mast, "Empirical Relationships Between Acoustic Parameters in Human Soft Tissues," Acoust Research Letters Online, Nov. 16, 2000, pp. 37-42.
Masugata et al., "Relationship Between Myocardial Tissue Density Measured by Microgravimetry and Sound Speed Measured by Acoustic Microscopy," Ultrasound in Med & Biol 25(9) (1999) 1459-1463.
Metz, "Basic principles of ROC analysis"; Semin Nucl Med. Oct. 8, 1978 (4):283-98.
Metz, "Receiver Operating Characteristic Analysis: A Tool for the Quantitative Evaluation of Observer Performance and Imaging Systems"; J Am Coli Radiol 2006; 3: 413-422.
Metz, "ROC methodology in radiologic imaging"; Invest Radiol. Sep. 21, 1986 (9):720-33.
Miller et al., "Sonoporation of Cultured Cells in the Rotating Tube Exposure System," Ultrasound Med & Biol 25 (1999) 143-149.
Noble et al., "Spleen Hemostasis Using High-Intensity Ultrasound: Survival and Healing," J. Trauma Injury, Infection, and Critical Care 53(6) (2002) 1115-1120.
Ophir et al., "Elastography: Ultrasonic Estimation and Imaging of the Elastic Properties of Tissues," Proc Instn Mech Engrs 213(Part H) (1999) 203-233.
Palomares et al., "Mammographic Density Correlation with Gail Model Breast Cancer Risk Estimates and Component Risk Factors," Cancer Epidemiol Biomarkers Prev 15(7) (2006) 1324-1330.
Robinson et al., "Quantitative Sonography," Ultrasound in Med & Biol 12(7): 555-65 (1986).
Schmidt et al., "Modification of Kirchhoff migration with variable sound speed and attenuation for tomographic imaging of the breast," Proc. of SPIE vol. 7968, Mar. 25, 2011.
Singh, Seema et al. "Color Doppler Ultrasound as an Objective Assessment Tool for Chemotherapeutic Response in Advanced Breast Cancer." Breast Cancer, 2005, vol. 12, No. 1, 2005, pp. 45-51.
Teubner et al., "Comparative Studies of Various Echomammography," Ultraschall in Der Medizin 3(3) (1982) 109-18, G. Thieme Verlag, Stuttgart/New York.
Vaezy et al., "Real-Time Visualization of High-Intensity Focused Ultrasound Treatment Using Ultrasound Imaging," Ultrasound in Med & Biol 27(1) (2001) 33-42.
Walach et al., Local Tissue Attenuation Images Based on Pulsed-Echo Ultrasound Scans, IEEE Transactions Onbiomedical Engineering, vol. 36. No. 2, Feb. 1989.

(56) References Cited

OTHER PUBLICATIONS

Wei et al., "Correlation Between Mammographic Density and Volumetric Fibroglandular Tissue Estimated on Breast MR Images," Med Phys 31(4) (2004) 933-942.
Weiwad et al., "Direct Measurement of Sound Velocity in Various Specimens of Breast Tissue," Invest Radiol 35(12) (2000) 721-6.
Wolfe, "Risk for Breast Cancer Development Determined by Mammographic Parenchymal Pattern," Cancer 37(5) (1976) 2486-2493.
Xu, et al. "A Study of 3-Way Image Fusion for Characterizing Acoustic Properties of Breast Tissue." Medical Imaging 2008: Ultrasonic Imaging and Signal Processing. Feb. 16, 2008.
Yaffe, "Breast Cancer Risk and Measured Mammographic Density," Eur J Cancer Prevention 7(1) (1998) S47-55.
Yaman, C. et al., "Three-Dimensional Ultrasound to Assess the Response to Treatment in Gynecological Malignancies." Gynecologic Oncology, Academic Press, vol. 97, No. 2, May 1, 2005, pp. 665-668.
Yankelevitz et al., "Small Pulmonary Nodules: Volumetrically Determined Growth Rates Based on CT Evaluation," Radiology 217 (2000) 251-256.
Andre et al., "A New Consideration of Diffraction Computed Tomography for Breast Imaging: Studies in Phantoms and Patients," Acoustical Imaging, 21, 379 (1995).
Borup et al., "Nonperturbative Diffraction Tomography Via Gauss-Newton Iteration Applied to the Scattering Integral Equation," Ultrasonic Imaging 1, Academic Press, Inc., (1992), 69-85.
Candy et al., "Signal Processing: The Model-Based Approach," pp. 178-213, (McGraw Hill. 1986).
Dean, "The Radon Transform and Some of Its Applications," Krieger Publishing Company, Malabar, Florida (1993).
Greenleaf et al., "Introduction to Computer Ultrasound Tomography," Computer Aided Tomography and Ultrasonics in Medicine, (1979), North-Holland, 125-136.
Greenleaf et al., "Multidimensional Visualization of Ultrasonic Images," J Acoust Soc Amer, 95 (1994), 2902.
Greenleaf, "Tissue Characterization with Ultrasound: vol. II: Results and Applications," CRC Press, Inc., Boca Raton, Florida, pp. 95-122.
Harmuth, "Sequency Theory: Foundations and Applications, Advances in Electronics and Electron Physics," (Academic Press, 1977) 18-95.
Haykin, "Neural Networks—A Comprehensive Foundation," Prentice Hall, (1994), 236-284.
Hebden et al., "Acoustically Modulated Electrical Impedance Tomography," Proc SPIE, 1231 (1990), 7-14.
Johnson et al., "Comparison of Inverse Scattering and Other Tomographic Imaging Algorithms Using Simulated and Tank Data for Modeling Subbottom Imaging Systems," IEEE Oceans '93 Symposium, Nov. 1993, vol. 1, (1993), 458-462.
Johnson et al., "Modeling of Inverse Scattering and Other Tomographic Algorithms in Conjunction with Wide Bandwidth Acoustic Transducer Arrays for Towed or Autonomous Sub-bottom Imaging Systems," Proc. Mastering the Oceans Through Technology, Oceans Newport, Rhode Island, USA, Oct. 26-29, 1992, 294-299.
Li et al., Comparison of Ultrasound Attenuation Tomography Methods for Breast Imaging, Medical Imaging 2008: UltrasonicImaging and Signal Processing, Proc. of SPIE., vol. 6920, 692015-(1-9), 2008.
Mitchell, An Introduction to Genetic Algorithms, pp. 8-11. 35-78. 155-179 (MIT Press, 1996).
Nelson et al., "Interactive Acquisition, Analysis and Visualization of Sonographic Volume Data," International J Imaging Sys and Tech, 8(26), (1997), 26-37.
Sehgal et al., "Visualization of Breast Calcification by Acoustic Resonance Imaging," Radiology Supplement, 84th Scientific Assembly and Annual Meeting, Nov. 29-Dec. 4, 1998 presented in McCormick Place, Chicago, Illinois, vol. 209, listing: 1150 (1998).
Shi et al., "Effects of Pressure Changes on Harmonic and Subharmonic Response of US Contrast Microbubbles," 84th Scientific Assembly and Annual Meeting, Nov. 29-Dec. 4, 1998, presented in McCormick Place, Chicago, Illinois, vol. 209, listing: 1154 (1998).
Wiskin et al., "Full Inverse Scattering vs. Born-like Approximation for Imaging in a Stratified Ocean," Proc. Eng. in Harmony with the Ocean, (Oceans '93), Victoria, British Columbia (Oct. 1993).

* cited by examiner

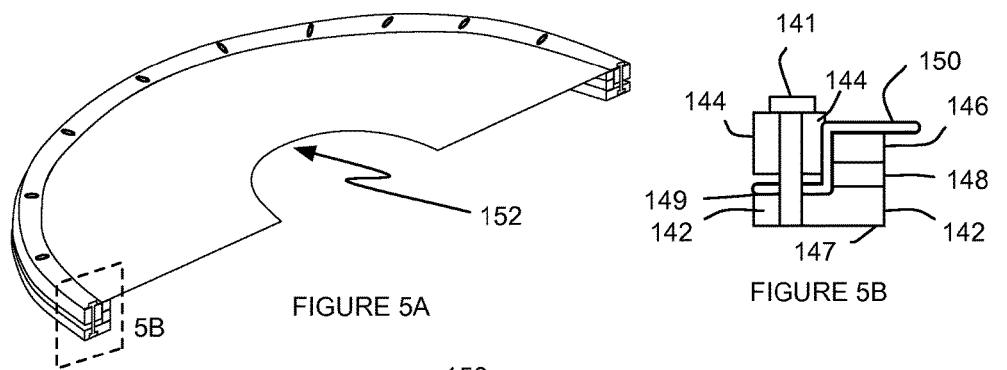
FIGURE 5A
FIGURE 5B
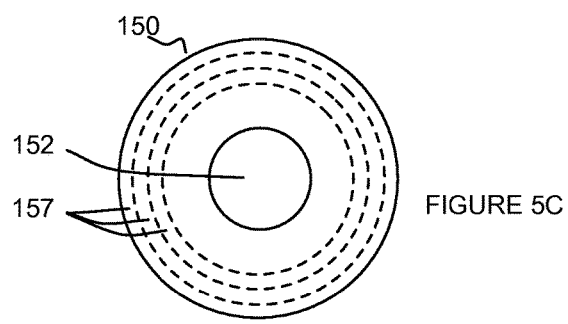
FIGURE 5C
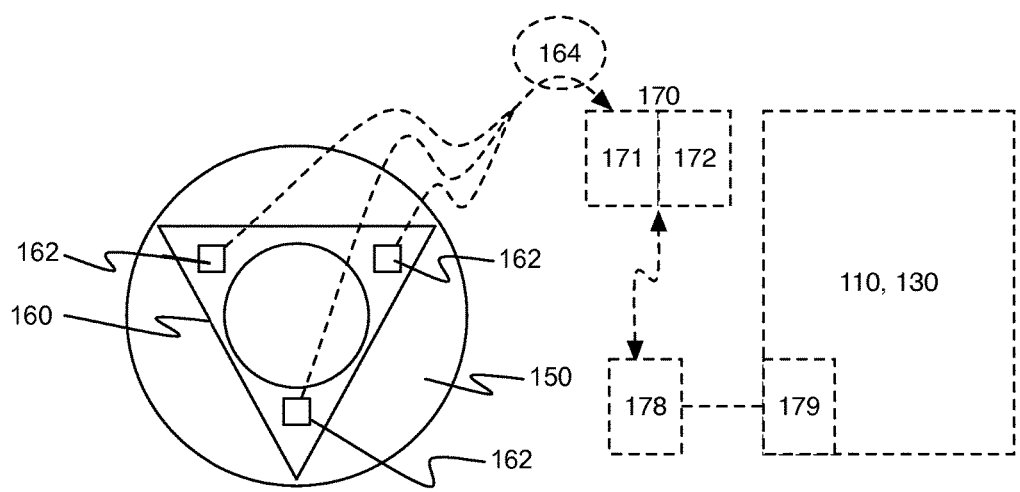
FIGURE 6

// PATENT SUPPORT SYSTEM

CROSS-REFERENCE TO RELATED APPLICATIONS

This application claims the benefit of U.S. Provisional Application Ser. No. 61/778,985 filed Mar. 13, 2013, which is incorporated in its entirety herein by this reference.

TECHNICAL FIELD

This invention relates generally to the medical technology field, and more specifically to a new and useful patient interface system in the medical technology field.

BACKGROUND

Early detection of breast cancer and other types of cancer typically result in a higher survival rate. Despite a widely accepted standard of mammography screenings for breast cancer detection, there are many reasons that cancer is often not detected early. One reason is low participation in breast screening, as a result of factors such as fear of radiation and discomfort. In particular, the mammography procedure involves compression of the breast tissue between parallel plates to increase the X-ray image quality by providing a more uniform tissue thickness and stabilizing the tissue. However, this compression is typically uncomfortable, or even painful. Mammography has additional drawbacks, such as limited performance among women with dense breast tissue and a high rate of "false alarms" that lead to unnecessary biopsies that are collectively expensive and result in emotional duress in patients.

Ultrasound tomography is one imaging modality in development that may be a practical alternative to mammography. However, there is a need to create a new and useful patient interface system for scanning a volume of tissue in this manner that is safe and comfortable for patients. This invention provides such a new and useful patient interface system.

BRIEF DESCRIPTION OF THE FIGURES

FIGS. 5A and 5B are a perspective cross-sectional view of a schematic of the support assembly and a cross-sectional view of a schematic of the frame of the support assembly, respectively, of an embodiment of the patient interface system;

FIG. 5C is a top view of an embodiment of a portion of the support assembly; and FIG. 6 is a schematic of a pressure sensor array in a variation of the patient interface system.

DESCRIPTION OF THE PREFERRED EMBODIMENTS

Figure 1A:
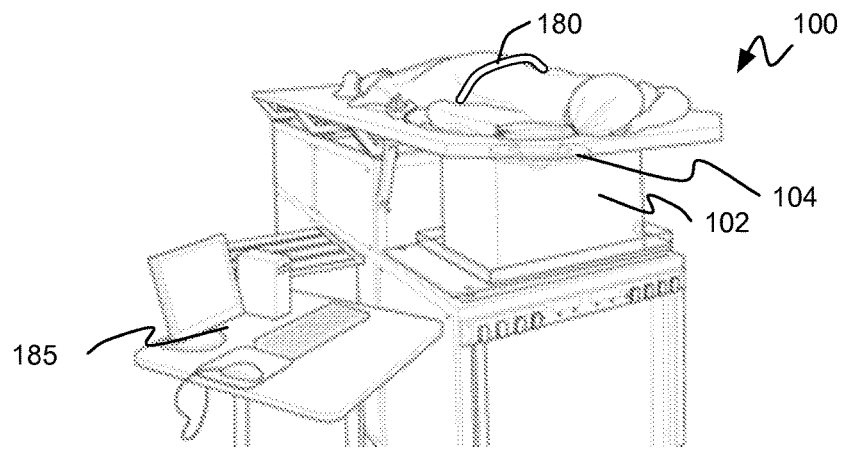
FIG. 1A is an overall perspective view of a schematic of an embodiment of the patient interface system.

The following description of preferred embodiments of the invention is not intended to limit the invention to these preferred embodiments, but rather to enable any person skilled in the art to make and use this invention.

1. System

As shown in FIGS. 1A-3, an embodiment of a patient interface system 100 for scanning a volume of tissue protruding from a patient includes: a base 110 including a planar portion 112 on which the patient can lie prone and a frustoconical portion 120 with a sloped inner surface 122 and defining a base aperture 114 configured to receive the volume of tissue; and a support assembly 130 coupled to the base 110 including a frame 140 and membrane 150 disposed within the frame 140 and defining a membrane aperture 152 aligned with the base aperture 114 for receiving the volume of tissue. The frame 140 of the support assembly 130 is preferably coupled to the frustoconical portion 120 of the base and preferably surrounds the base aperture 114. The membrane 150 of the support assembly 130 is preferably disposed within the frame 140 and configured to conform to the body wall of the patient (thereby increasing access to the volume of tissue) and deflect into the sloped inner surface of the base in response to weight of the patient. In one embodiment, the support assembly 130 and/or membrane 150 can be selected from a set of support assemblies and/or membranes that are sized differently (e.g. different sizes of membrane aperture 152) to allow optimization for patients of differing builds. The system 100 can further include a table topper 116 configured to couple to planar portion 112 of the base 100, and a pressure sensor array 160 distributed proximal to a patient contact surface of the support assembly 130, wherein the pressure sensor array 160 is configured to generate signals that facilitate patient alignment in response to the weight of the patient. In still other embodiments, the system 100 can additionally include a processor 170 configured to generate an analysis based upon signals generated by the pressure sensor array 160, and a retaining module 180 configured to retain the patient in a desired configuration at the patient interface system 100.

Figure 1B:
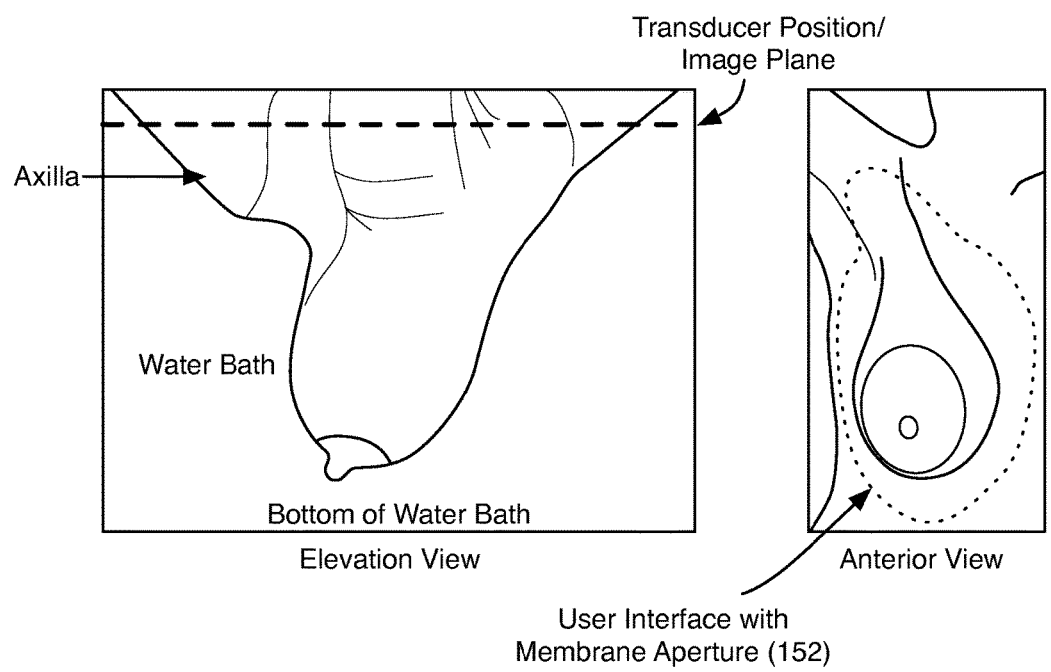
FIG. 1B depicts an elevation view of a pendulous breast interfacing with an embodiment of the system.
Figure 1C:
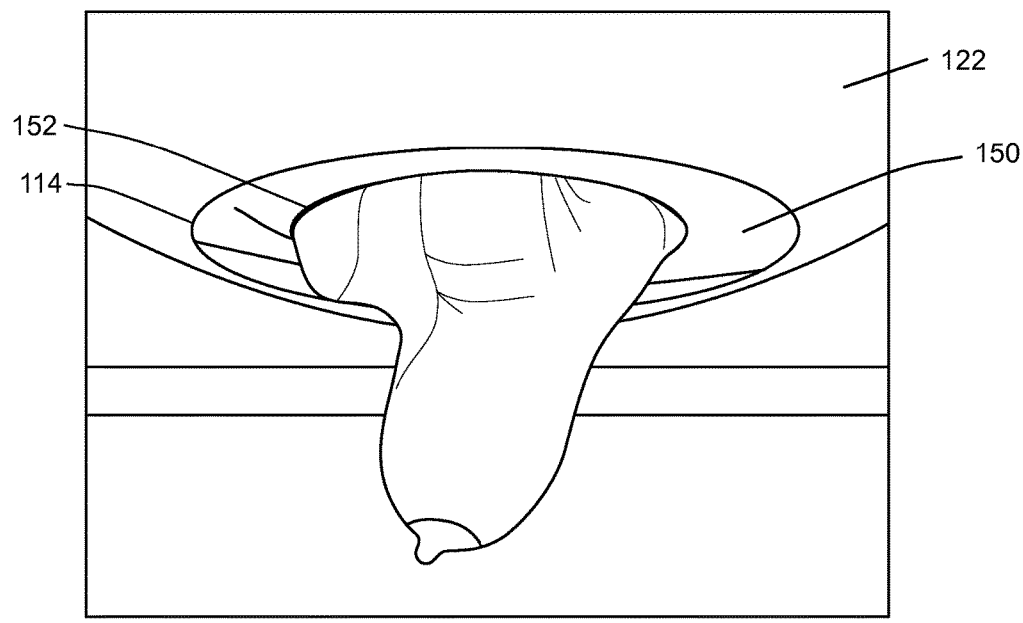
FIG. 1C depicts a side view of a pendulous breast interfacing with an embodiment of the system, including exposure of a patient's axilla and chest wall through a taut membrane.

The patient interface system 100 functions to position a patient and volume of tissue in place for an image scan, in order to ensure proper patient positioning and to facilitate a reduction in the amount of unnecessary scans taken (e.g., due to patient misalignment). In one embodiment, as shown in FIGS. 1A, 1B, 1C, and 2A, the patient interface system 100 is configured to be placed over an ultrasound imaging tank 102, which receives the volume of tissue extending through the membrane and base apertures 114,152 during an ultrasound tomographic scan, such as for imaging breast tissue or any other suitable volume of tissue that can extend through the table aperture 114 and membrane aperture 152. As shown in FIGS. 1B and 1C, embodiments of the system 100 preferably allow access to a patient's chest wall and axilla, in order to facilitate scanning of a protruding tissue of the patient (e.g., breast tissue0. In particular, the patient interface system 100 preferably allows a ring transducer 104 surrounding the extended breast tissue to have more complete access to the tissue up to the chest wall of the patient. The ring transducer 104 can be a ring transducer 104 as described in U.S. application Ser. No. 13/756,851 entitled "System and Method for Imaging a Volume of Tissue" and filed on Feb. 1, 2013, which is incorporated herein in its entirety by this reference, or any other suitable ring transducer 104. Furthermore, embodiments of the system 100 can enable access to and scanning of any other suitable tissue of a patient.

The patient interface system 100 is preferably modular to provide a customizable interface for various patients of differing builds, and comfortable for patients to encourage regular screenings and early cancer detection. The patient interface system 100 can alternatively be non-modular. Additionally, the patient interface system 100 can be used in conjunction with any suitable imaging modality, or for any suitable purpose involving substantially complete access to volume of tissue (e.g., for scanning using another imaging modality, for biopsy, for surgical procedures, etc.).

The base 110 functions to support the weight of a prone patient, and is preferably configured to provide a surface that spans the entire height and width of the patient, such that the patient's entire body can be supported within the surface of the base. However, the base no can alternatively be configured to provide a surface that is shorter that the height of the patient and/or narrower than the width of the patient, such that portions of the patient's body are not supported by the base no. The base 110 preferably includes a planar portion 112 on which the patient can lie prone, and a frustoconical portion 120 with a sloped inner surface 122 configured to provide comfort and allow the volume of tissue to extend into the base aperture 114. As such, the frustoconical portion 120 preferably terminates at the base aperture 114, which provides an opening into the ultrasound imaging tank 102 configured to receive the volume of tissue and facilitate scanning of the volume of tissue. The base aperture 114 is preferably circular, but in alternative configurations, the base aperture 114 can alternatively be ellipsoidal, oblong, polygonal, or any other suitable shape. In variations, the frustoconical portion 120 and the base aperture 114 are preferably configured to receive and accommodate a single breast of the patient; however, in other variations, the base 110 can be configured to accommodate two breasts and/or multiple protruding tissues (e.g., a face, knees, buttocks, etc.) of the patient, for example, by way of multiple apertures, multiple frustoconical portions, multiple portions displaced from the planar portion 112 of the base, and/or any other suitable element(s) configured to accommodate multiple tissue volumes of the patient. Furthermore, the base 110 can be configured to accommodate a head region of a patient, for instance, with an aperture configured to receive and support a region of a patient's head or face (e.g., a coronal region, a sagittal region, a horizontal region, etc.), as the patient interfaces with the base no (e.g., in configuration wherein the patient is lying face down, lying on his/her side, lying face up, and/or in any other configuration).

The planar portion 112 and frustoconical portion 120 are preferably separate pieces configured to couple to one another, through complementary nesting (e.g., frustoconical portion 120 seated within a recessed cavity or on a shelf of the planar portion 112), interlocking joints, fasteners, by press fit, using adhesives, using magnets, using thermal bonding, or in any suitable manner. In variations wherein the planar portion 112 and the frustoconical portion 120 are configured to couple to one another, the planar portion 112 and the frustoconical portion 120 can thus be configured to permanently couple to each other, or can be configured to reversibly couple to each other. In variations involving reversible coupling, the frustoconical portion 120 can be a substitutable portion, such that different frustoconical portions 120 corresponding to different patient morphologies can be provided at the base 110 to enhance patient comfort. Alternatively, the frustoconical portion 120 can be integrally formed (e.g., physically coextensive, of unitary construction) with one or more parts of the planar portion 112 of the base 100, for example, by casting. Furthermore, in some variations, the base no can include any one or more of: a planar surface, a contoured surface (e.g., to a patient's body), frustoconical surface, and any other suitable surface of combination of surfaces to suitably support a particular patient size or shape.

Figure 2A:
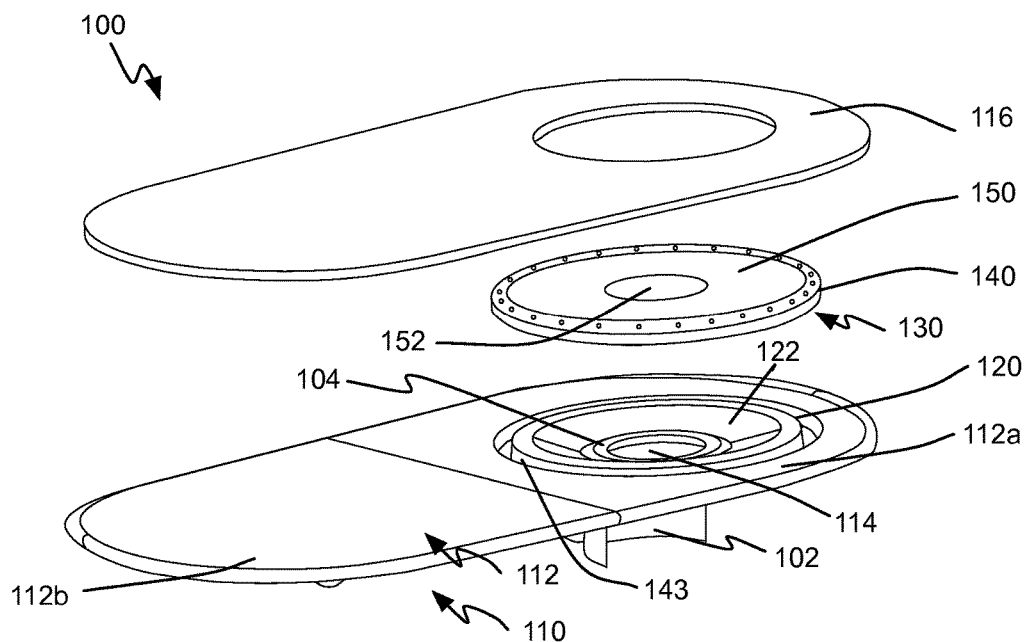
FIG. 2A is an exploded view of a schematic of an embodiment of the patient interface system.
Figure 2B:
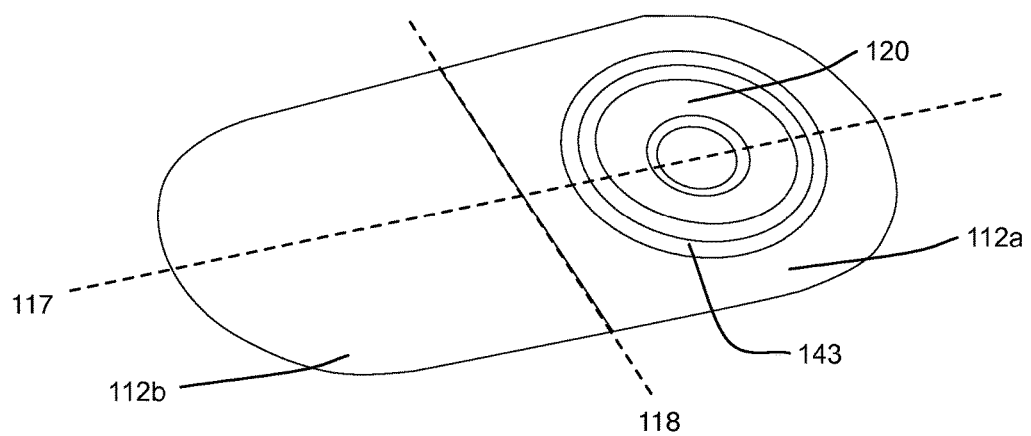
FIG. 2B is a top view of a portion of an embodiment of the patient interface system.
Figure 2C:
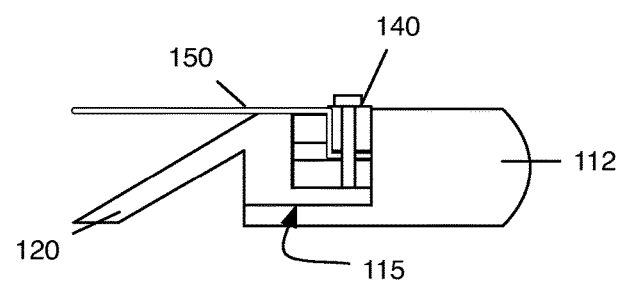
FIG. 2C is a side cross-sectional view of a schematic of an embodiment of the patient interface system.

In one variation, as shown in FIG. 2B, the base 110 is divided along at least one of a long axis 117 and a short axis 118, such that the planar portion 112 includes two halves, including a head portion 112a configured to support a superior portion of the patient (e.g., torso, arms, and head) and a foot portion 112b configured to support an inferior portion of the patient (e.g., legs and feet). However, the planar portion 112 of the base no can alternatively include two unequally sized pieces (e.g., with a relatively longer head portion 112a or a relatively longer foot portion 112b), or fewer or more than two pieces (e.g., pieces that allow customization of the base to support the user's limbs in different configurations, and/or multiple pieces that allow for angular/linear displacement of portions of the base no at multiple points along the base). As shown in FIG. 2C, the head portion 112a of the base preferably includes a region 115 that receives or is coupled to the frustoconical portion 120 and/or the support assembly 130 placed on top of the base no. The planar portion 112 is preferably configured to be oriented in a substantially horizontal configuration, but in alternative variations, any portion of the base no can be oriented in and/or adjustable to any suitable relative angle, such as to increase patient comfort or to increase access to areas of the patient that are otherwise difficult to access. For instance, the base no and/or the planar portion 112 can be oriented in a substantially vertical configuration (e.g., to form a 75-90° angle in relation to a horizontal plane) for patient comfort (e.g., for patients with back issues). The base no and/or the planar portion 112 can additionally or alternatively be transitioned into a substantially vertical configuration (e.g., to form a 75-90° angle in relation to a horizontal plane) or any other configuration for patient loading, and then transitioned into a desired configuration (e.g., a horizontal configuration) after patient loading, to facilitate imaging in any suitable configuration.

Figure 3:
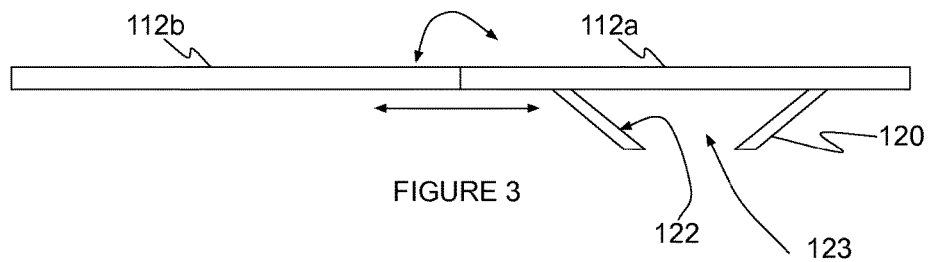
FIG. 3 is a side view of a schematic of the base of an embodiment of the patient interface system.

In some embodiments, as shown in FIG. 3, the relative positions and orientations of multiple portions of the base 110 can be adjusted. In one variation, multiple portions can be coupled to one another in such a manner to allow expansion (e.g., linear expansion) or contraction to accommodate taller or shorter patients. For example, multiple portions of the base 110 can be slidingly coupled to one another or to a common track (or in any suitable adjustable manner). As another example, additional separate portions of the base 110 can be added or removed from a series of base portions to extend or shorten the length of the base no, such as in the manner of a "drop leaf" table. In this example, each base portion in the series of base portions can include grooves or other features (e.g., protrusions, recesses) that facilitate alignment, and can additionally or alternatively include couplers (e.g., magnetic couplers, locks, straps, brackets, screws, pins, etc.) that reversibly maintain the position(s) of the base portion(s). In another variation, multiple portions can be coupled with a hinge or common adjustable framework (or in any suitable adjustable manner)

to allow angular adjustment of at least part of the base no. The adjustable framework can be manually or automatically actuated using an actuator, such as a ratchet mechanism and/or motor (e.g., in response to signals generated by the pressure sensor array 160 described below). In examples, the head portion 112a and the foot portion 112b can thus be angularly displaced relative to each other about an axis (e.g., the short axis 118), in order to tilt the head portion 112a and/or the foot portion 112b into inclining and/or declining configurations. In any of these variations, the base 110 preferably includes a lock (e.g., pin, friction lock, or any suitable mechanism) that secures the multiple portions in their relative positions and orientations in a reversible manner. Furthermore, still other variations of the base 110 can additionally or alternatively include multiple sections that can be linearly and/or angularly displaced about any suitable axis at any suitable number of positions along the base no.

The planar portion 112 of the base preferably includes a rigid material that is compliant with the U.S. Food and Drug Administration (FDA) guidelines; for instance, in a specific example, the planar portion 112 of the base includes Corian® surfaces (e.g., Corian® Whisper surfaces manufactured by DuPont™) that are compliant with FDA regulation 1770.1010. The material is preferably biocompatible, non-porous, and sanitizable. Furthermore, the material of the planar portion 112 preferably does not interfere with ultrasound signals transmitted and received using a transducer proximal to the base no and/or the volume of tissue. In other variations, however, the material of the base 110 can be configured to facilitate reflection of transmitted ultrasound signals in order to enable enhanced analyses of acoustomechanical properties of the volume of tissue, and/or to function as a shield to protect a patient against, for example, harmful types of radiation (e.g., x-ray radiation). However, the planar portion 112 of the base can additionally or alternatively include any other suitable weight-supportive, biocompatible material.

The frustoconical portion 120 of the base 110 functions to provide a recessed space into which the membrane 150 of the support assembly 130 can deflect, particularly when the membrane 150 of the support assembly 130 supports the body wall of the patient. The frustoconical portion 120 is preferably configured to extend beyond a plane defined by the planar portion 112 of the base 110, and can at least partially define the base aperture 114 configured to receive the volume of tissue. As shown in FIGS. 2A and 3, the frustoconical portion 120 is preferably in the approximate shape of a funnel, including a sloped inner surface 122 extending between a narrow end terminating at an opening 123 and a wider end opposed to the narrow end. The sloped inner surface 122 is preferably linearly sloped from the wider end to the narrower end, and in a specific example defines a slope relative to a horizontal plane of between 20 and 60 degrees. However, the sloped inner surface 122 can alternatively include any suitable curvature and/or combination of a curved slope and a linear slope. The frustoconical portion 120 is preferably oriented such that the narrow end of the frustoconical portion 120 is located below the wider end, in the orientation shown in FIG. 2A. In one variation in which the planar portion 112 and the frustoconical portion 120 of the base 110 are separate pieces, the planar portion 112 and the frustoconical portion 120 each preferably define respective, aligned base apertures 114 through which the volume of tissue can protrude and be accessible from the underside of the base 110, in the orientation shown in FIG. 2A. For example, alignment of the apertures 114 can be facilitated by the frustoconical portion 120 nesting within a complementary region of the planar portion 112, mechanical alignment keys, visual markings, magnetic elements that facilitate alignment, and/or any suitable features.

Similar to the planar portion 112 of the base 110, the frustoconical portion 120 preferably includes a rigid material that is compliant with the U.S. Food and Drug Administration (FDA) guidelines. In a specific example, the frustoconical portion 120 includes a polyethylene terephthalate glycol-modified (PETG) surface such as a surface manufactured by Curbell Plastics™ (e.g., Spectar®/Vivak® surfaces manufactured by Curbell Plastics™). In another specific example, the frustoconical portion 120 of the base 110 can include Corian® surfaces (e.g., Corian® Whisper surfaces manufactured by DuPont™ that are compliant with FDA regulation 1770.1010. The material is preferably biocompatible, non-porous, and sanitizable. Furthermore, the material of the frustoconical portion 120 preferably does not interfere with ultrasound signals transmitted and received using a transducer proximal to the base no and/or the volume of tissue. In other variations, however, the material of the base no can be configured to facilitate reflection of transmitted ultrasound signals in order to enable enhanced analyses of acoustomechanical properties of the volume of tissue and/or to function as a shield to protect a patient against, for example, harmful types of radiation (e.g., x-ray radiation). However, the frustoconical portion 120 of the base no can additionally or alternatively include any other suitable weight-supportive, biocompatible material that can be processed to form the frustoconical portion 120.

In one specific example, as shown in FIGS. 2A and 2B, the base no defines a symmetric obround surface with a long axis 117 and a short axis 118, wherein the frustoconical portion 120 is biased toward an end of the long axis 117, in order to accommodate a volume of breast tissue of a prone patient interfacing with the system 100. In the specific example, the frustoconical portion 120 is aligned with the long axis 117, such that the long axis 117 defines an axis of symmetry for the base aperture 114. In this example, the base 110 is configured to be wider than the width of the patient, such that the patient can shift his/her lateral position relative to the long axis 117 in order to pass each breast through the medially positioned base aperture 114. Furthermore, in the specific example, the base no is configured to be adjustable at the short axis 118, such that the short axis 118 defines two halves of the base no that can be adjusted and manipulated relative to each other (e.g., as in FIG. 3) in order to provide multiple configurations (e.g., tilted configurations, expanded configurations, contracted configurations) that can customize the base no to the patient's body and/or provide better access to the volume of tissue. However, in variations of the specific example, the frustoconical portion 120 can be unaligned with the long axis 117 (e.g., to target a right or left breast of the patient in a customizable manner), such that the frustoconical portion 120 is biased in one direction along an axis parallel to the short axis 118 (e.g., in order to accommodate one breast or the contralateral breast), and/or the base 100 can be unadjustable at the short axis 118 to provide a fixed configuration of the base no. In further variations of the specific example, the frustoconical portion 120 can be adjustable in a direction parallel to the short axis 118 and/or the long axis 118 (e.g., using a sliding track) in order to accommodate a single breast of the patient in one configuration, and a contralateral breast of the patient in another configuration of the frustoconical portion 120.

Figure 4:
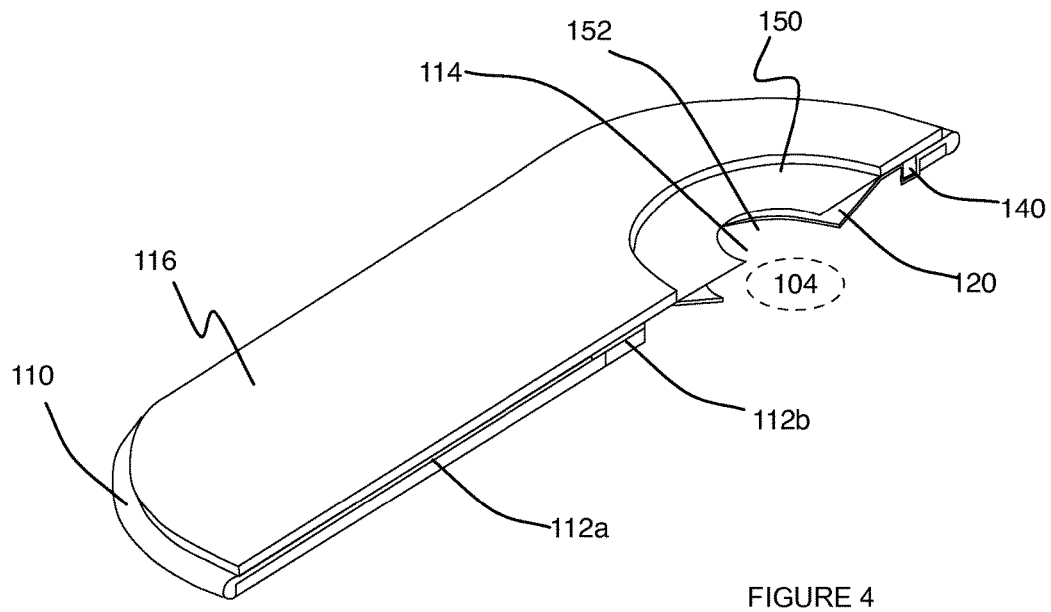
FIG. 4 is a perspective cross-sectional view of a schematic of an embodiment of the patient interface system.

In some embodiments, the system 100 can additionally include a table topper 116 disposed on the planar portion 112 of the base 110. As shown in FIGS. 2A and 4, the table topper 116 can be processed to match the footprint of the base 110, including an aperture to expose the support assembly 130. However, the aperture of the table topper can alternatively be configured to hide all or a portion of the support assembly 130. In one variation, the table topper 116 includes a cushion, such a foam pad (e.g., memory foam) or suitable upholstered cushioning, that provides a comfortable surface for the patient to lie down on. In one example, the table topper 116 includes a planar slab of medical foam processed (e.g. formed, cut, molded, etc.) to match the footprint of the base no. In other variations, the table topper 116 additionally or alternatively includes a contoured, substantially non-planar surface that can position the patient into a more ergonomic or comfortable body position, and/or can position the patient such that the breast tissue is in better position for scanning. In examples of these variations, the table topper 116 can be processed to define recessed and/or protruding regions for any one or more of: the patient's chest, the patient's abdomen, the patient's knees, the patient's feet, and any other suitable body party of the patient.

The table topper 116 can additionally be one of a set of multiple table toppers of various sizes, such that a particular table topper can be substituted in a modular manner into the patient interface system 100 to optimally accommodate patients of various morphologies. In alternative variations, the table topper 116 can include a particulate and/or pliable filling that can be manipulated (e.g., molded) to accommodate different users. As such, the particulate filling can be pushed around or molded, for example, within a casing, in order to mold the table topper 116 to the patient's body. The table topper 116 preferably includes an external non-porous surface that can easily be disinfected or wiped clean between patients (e.g., vinyl). However, the table topper 116 can additionally or alternatively be additionally covered with a protective cover that can be disposed of and replaced by a new cover after a patient interfaces with the patient interface system 100.

In a specific example, the table topper 116 includes a polyurethane foam encased within a vinyl covering, wherein the polyurethane foam and the vinyl covering are compliant with the U.S. Food and Drug Administration (FDA) guidelines. The polyurethane foam is processed to be water repellant, and is biocompatible and sanitizable. Furthermore, the material of the table topper 116 preferably does not interfere with ultrasound signals transmitted and received using a transducer proximal to the base 110 and/or the volume of tissue. In other variations of the specific example, however, the material of the table topper 116 can be configured to facilitate reflection of transmitted ultrasound signals in order to enable enhanced analyses of acoustomechanical properties of the volume of tissue, and/or can function as a shield in variations of the system 100 configured to interface with imaging modalities involving, for example, more harmful forms of radiation (e.g., x-ray radiation). However, the table topper 116 can additionally or alternatively include any other suitable conforming, biocompatible material that facilitates patient comfort when interfacing with the system 100.

The support assembly 130 functions to simultaneously facilitate patient comfort and to allow a volume of tissue of the patient to extend through the base aperture 114 into a tank 102 for tissue scanning. The support assembly 130 includes a frame 140 and a membrane 150 disposed within the frame 140 and configured to conform to the body wall and deflect into the inner surface of the frustoconical portion 120 of the base 110. Preferably, the support assembly 130 is configured to couple to the base 110 such that a membrane aperture 152 of the membrane 150 is aligned with the base aperture 114, and such that a volume of tissue of the patient can pass through both the membrane aperture 152 and the base aperture 114. The support assembly 130 can be one of a set of multiple support assemblies that include membrane apertures of various sizes and/or locations relative to the frame 140, such that a particular support assembly 130 can be reversibly substituted in a modular manner into the patient interface system 100 to accommodate variations in patient morphology. For example, a first support assembly 130 can include a larger membrane aperture 152 for scanning a breast of a patient with larger breasts, and a second support assembly 130 can include a smaller membrane aperture 152 for scanning a breast of a patient with smaller breasts. In other variations, however, the support assembly 130 can be a non-substitutable element of the system 100, and can still accommodate variations in patient morphology in any other suitable manner. For instance, the support assembly 130 can include a set of pre-cut inserts (e.g., inserts with different sized apertures, inserts with different material properties, etc.) that can be positioned superior to or inferior to the membrane 150 and aligned relative to the membrane aperture 152 in any suitable manner, in order to accommodate different sized breasts without requiring the tension of the membrane to be adjusted. In still other variations, however, the support assembly 130 may not be configured to accommodate variations in patient morphology.

In another example, different support assemblies 130 can include different numbers and/or configurations of membrane apertures 152 for accommodating both breasts of a patient and/or other tissues of a patient. In an alternative variation, the patient interface system 100 includes a frame 140 and a membrane 150 that is one of a set of multiple membranes, such that a particular membrane 150 can be swapped in a modular manner to couple to the frame 140. In examples, a first membrane configured to be retained within the frame 140 can include a larger membrane aperture 152 for scanning a breast of a patient with larger breasts, and a second membrane configured to be substituted for the first membrane can include a smaller membrane aperture 152 for scanning a breast of a patient with smaller breasts. In another example of this alternative variation, membranes can include different numbers and/or configurations of membrane apertures 152 for accommodating both breasts of a patient and/or other tissues of a patient. Thus, in these alternative embodiments, the support assembly includes a single frame 140 and replaceable membranes 150 that are configured for different applications. However, the patient interface system 100 can include any suitable number of frames and/or membranes 150 that can be combined in any suitable manner to optimize position, comfort, and/or scanning access to the tissue for various patients.

The frame 140 of the support assembly 130 functions to provide structural support to the membrane 150 and couples the membrane 150 to the base no. The frame 140 can additionally function to maintain the membrane 150 in tension at a peripheral portion of the membrane 150, such that the membrane 150 provides a counteracting force in response to the weight of the patient's body. However, in some variations, the frame 140 may not be configured to retain the membrane 150 in tension. The frame 140 is preferably annular, forms a closed perimeter about the membrane 150, and can be circular or ellipsoidal; however, the frame 140 can alternatively form an open perimeter about a portion of the membrane 150 and/or define any other suitable shape (e.g., regular polygonal shape, irregular polygonal shape, irregular curvilinear shape).

As shown in FIGS. 5A and 5B, the frame 140 preferably includes at least a frame base 142, which functions to provide coupling locations to secure the membrane 150 to the frame 140 in a reversible manner. In some variations, the frame base 142 can additionally or alternatively function to provide surfaces that allow coupling of the membrane 150 to the frame 140 in a reversible manner. The frame base 142 preferably couples to or abuts the frustoconical portion 120 of the base no at an inferior surface 147 of the frame base 142, but can additionally or alternatively couple to the planar portion 112 or other suitable portion of the base no. In one example, as shown in FIGS. 2A-2C and 5A-5B, the frame base 142 is preferably annular and configured to nestle and be seated within an annular recess 143 formed circumferentially between the frustoconical portion 120 and the planar portion 112 of the base 110, such that an inferior surface of the frame base 142 abuts the frustoconical portion 120. In the example, the frustoconical portion 120 is configured to define two perpendicular walls of the annular recess 143, and the planar portion 112 is configured to define a third wall of the annular recess 143, wherein the third wall is substantially opposed to and/or concentric with one of the walls defined by the frustoconical portion 120. However, the frame base 142 can alternatively be configured to be seated within an annular recess defined circumferentially in the frustoconical portion 120, within an annular recess defined circumferentially in the planar portion 112 of the base no, or within a recess defined by the frustoconical portion 120 and/or the planar portion 112 in any other suitable manner. In some variations of the example, the recess and/or corresponding mating portion of the frame base 142 can be non-annular, the frame base 142 can be configured to only be partially seated within the recess, and the frame base 112 and the recess can be configured for coupling in any other suitable manner. In still other variations, the frame base 142 can couple to the base no with a snap fit, press fit, friction fit, latches, straps, magnetic elements, and/or in any suitable manner. Furthermore, the frame base 142 and/or the base no can include alignment features to orient the support assembly 130 in a particular matter relative to the base no. Such alignment features can include, for example, visual markings or physical interference features (e.g., ellipsoidal shape of the frame, mechanical keys, magnetic aligners). In a specific example, the frame base 142 includes a rigid polymer, such as polyethylene terephthalate glycol-modified (PETG), but can additionally or alternatively include any suitable material. In one embodiment, the frame base 142 can be injection-molded, but can alternatively be milled, 3D-printed, casted, or manufactured in any suitable manner.

The membrane 150 is preferably coupled in tension across the frame 140 of the support assembly 130 and configured to be positioned over the frustoconical portion 120 of the base no when the support assembly 130 is coupled to the base no, and preferably defines a membrane aperture 152 that receives the volume of tissue. In one variation, the membrane 150 includes a flexible polymer such as urethane and can be coupled to the support assembly 130 using, for example, mechanical fasteners, an adhesive, coupling using magnetic elements, and/or thermal welding. However, the membrane 150 can alternatively include any suitable material and be coupled with any suitable table fixation method. When a patient lies prone on the table surface and the volume of tissue (e.g., a volume of breast tissue) extends through the membrane aperture 152, the membrane 150 preferably deflects downward into the inner sloped surface 122 of the frustoconical portion 120 of the base no and conforms to the body wall around the volume of tissue, due to the weight of the patient on the support assembly 130. The membrane 150 is preferably one of a set of membranes with varying dimensions, such as in size, shape (e.g., circular, ellipsoidal, rectangular), number of apertures, and location (e.g., centered or off-centered relative to the frame 140 or relative to the base no) of the membrane aperture 152. The set of membranes can additionally or alternatively vary in any suitable aspect, such as material type or thickness. For example, material type can vary to accommodate patients with skin contact allergies, or can be stronger (e.g., have a higher tensile modulus, have greater fracture resistance) to provide extra patient support without requiring a substantially thicker membrane 150.

As shown in FIG. 5B, the support assembly 130 can further include a bezel 144 or rim coupled to the frame base 142 (e.g., a superior surface of the frame base 142) and circumferentially surrounding the membrane 150. The bezel 144 functions to facilitate coupling of the membrane 150 to the frame 140, such that the membrane 150 can be retained between the frame base 142 and the bezel 144 at a peripheral portion of the membrane 150. The bezel 144 is thus preferably a separate piece from the frame base 142, but can alternatively be integrally formed with the frame base 142 or other component of the support assembly 130 in a manner that allows a portion of the membrane 150 to be seated between the bezel and the frame base 142 or other component of the support assembly 130. For example, the bezel 144 and the frame base 142 can be integrally formed along an edge, in a manner that provides a circumferential gap between the bezel 144 and the frame base 142, wherein the circumferential gap can receive the membrane 150.

The bezel 144 is preferably proximal to a superior surface 149 of the frame base 142 by a series of rivets or other mechanical fasteners 141 distributed around the border of the support assembly 130. The rivets/mechanical fasteners can provide a compressive force that retains the membrane 150 between the bezel 144 and the frame base 142, and/or can pass through openings in the membrane 150 to lock the membrane in place relative to the bezel 144 and the frame base 142. The series of mechanical fasteners 141 are preferably arranged uniformly about the border of the support assembly 130, but can additionally or alternatively include fasteners that are clustered or randomly distributed about the border of the support assembly 130. For example, in one variation, a series of mechanical fasteners sandwiches the membrane 150 between the bezel 144 and the frame base 142, thereby securing the membrane 150 to the support assembly 130. However, the series of mechanical fasteners may not provide a compressive force, but may instead bias the bezel 144 toward the frame base 142 while coupling a peripheral portion of the membrane 150 between the bezel 144 and the frame base 142 (e.g., a fastener can be configured to pass through an opening in the membrane that is aligned with openings in the bezel 144 and the frame base 142). Additionally or alternatively, the bezel 144 can couple to the frame 140 with a snap fit, an adhesive, magnetic couplers, or any suitable fastening mechanism. The bezel 144 preferably includes the same material as the frame base 142, but can alternatively include one or more materials that are different from the frame base 142.

In one variation, as shown in FIG. 5B, the support assembly 130 can also include a tensioning ring 146, disposed adjacent to the membrane 150, at a radially inner side of the bezel 144 for maintaining the tension across the membrane 150. In particular, the tensioning ring 146 is preferably arranged concentrically with the frame base 142 and/or bezel 144 and underneath the membrane 150 in the orientation shown in FIG. 5B, such that the membrane 150 is stretched in suitable tension to support the patient weight. As such, in the orientation shown in FIG. 5B, a peripheral portion of the membrane 150 is retained between the tensioning ring 146 and the bezel 144 in order to maintain tension across the membrane 150.

The amount of membrane tension can be fixed and dependent on, for example, the thickness of the tensioning ring 146, and/or of a spacer 148 configured to displace the tensioning ring 146 from the frame base 142, wherein an increased height of the spacer 148/tensioning ring 146 can result in greater tension and a decreased height of the spacer 148/tensioning ring 146 can result in reduced tension. In some variations, the tensioning ring 148 and/or the spacer 148 can be substitutable elements, such that the amount of tension across the membrane can be manipulated by using tensioning rings 146 and/or spacers 148 of different thicknesses. The spacer 148 is preferably annular and configured to match a footprint of the tensioning ring 146; however, the spacer 148 can alternatively be defined by any other suitable geometry and/or footprint. For example, the spacer 148 can define a non-continuous surface that abuts the tensioning ring 146 at certain locations. The amount of membrane tension can additionally or alternatively be adjustable, such as to maintain a particular desired amount of tension over repeated stress on the membrane 150 due to repeated uses of the support assembly 130. For example, the thickness or elevation of the tensioning ring 146 and/or of the spacer 148 can be adjusted (e.g., using a mechanism to expand the thickness of the tensioning ring 146 and/or the spacer 148) to obtain a suitable amount of membrane tension. The tensioning ring 146 and/or spacer 148 can include the same material as the frame base 142, but can alternatively include one or more materials that are different from the frame base 142. The support assembly 130 can, however, include any other suitable element(s) for maintaining and/or adjusting tension across the membrane 150.

In a variation omitting a spacer 148, the membrane 150 can be configured to be retained at one of a set of peripheral regions 157, as shown in FIG. 5C, wherein each peripheral region of the set of peripheral regions 157 includes an annular band of the membrane 150. As such, retaining a radially inner band of the set of peripheral regions can contribute to increased tension across the membrane 150, and retaining a radially outer band of the set of peripheral regions can contribute to decreased tension across the membrane 150. As such, the membrane 150 can be retained at a peripheral region between the bezel 144 and the frame base 142, or in any other suitable manner. Furthermore, variations of the support assembly 130 can, however, include any suitable combination of the above described variations and examples. For example, a variation of the support assembly 130 can include a spacer 148 and a membrane 150 with a set of peripheral regions 157, such that the tension across the membrane 150 can be adjusted using at least one of two features. In still other variations, the system 100 can entirely omit elements that facilitate tensioning of the membrane 150. For example a patient's weight can provide an amount of tension that allows the patient's breast, axilla, and chest wall to protrude through the membrane aperture 152, in variations of the system 100 for imaging a volume of breast tissue.

In one embodiment of the system 100, as shown in FIG. 6, the support assembly 130 additionally includes an electrical subsystem coupled to the base 110 and/or support assembly 130. In one variation, the electrical subsystem can include a pressure sensor array 160 distributed on a patient contact surface of the support assembly 130. For example, the pressure sensor array 160 can be embedded in a sheet coupled to the frame base 142 and/or membrane 150, such that multiple pressure sensors 162 are distributed around the support assembly 130 and are configured to generate signals in response to the patient's weight and/or in response to a distribution of the patient's weight across the membrane 150. The sheet can include a flexible polymer such as urethane, preferably similar to the membrane 150. However, the pressure sensor array 160 can be configured relative to the frame base 142 and/or the membrane 150 in any other suitable manner. Furthermore, the pressure sensor array 160 can include any suitable number of pressure sensors in any suitable configuration (e.g., evenly distributed, distributed in a clustered manner, distributed randomly, distributed in a radial configuration, etc.) relative to the base 110 and/or the support assembly 130.

In some variations, the electrical subsystem can include a conditioning module 164, which functions to preprocess signals generated by the pressure sensor array 160 prior to transmission to a processor 170. The conditioning module 164 preferably comprises signal conditioning elements, including one or more of: an analog-to-digital converter (e.g., to convert analog signals from the pressure sensor array 160), an amplifier, and a filter for processing signals prior to transmission. In some variations, the conditioning module 164 can include a microprocessor configured to direct signal conditioning functionalities of the conditioning module 138 and a voltage regulator configured to protect elements of the electrical subsystem from overvoltage and/or under-voltage states.

In one variation, the pressure sensor array 160 can be used to confirm application of approximately uniform pressure at the membrane 150 (e.g., at a peripheral portion of the membrane, across the membrane) from the patient weight. For example, the pressure sensor array 160 can be used to confirm that the body wall of the patient is seated as evenly on the membrane 150 as possible and the volume of tissue is extended as fully as possible through the membrane aperture 152, thereby facilitating a complete imaging scan of the volume of tissue. Alternatively, the pressure sensor array 160 can be calibrated to a certain non-uniform pressure distribution that provides a desired patient configuration relative to the patient interface system 100, which can be used to maintain any suitable position of the patient to achieve good scanning results. In still other variations, the pressure sensor array 160 can be used for any suitable purpose, or variations of the system can entirely omit the pressure sensor array 160. Furthermore, the electrical subsystem can additionally or alternatively include any other suitable electrical components.

In variations of the system 100 including a pressure sensor array 160, the system 100 can include a processor 170, which functions to receive a set of signals from the pressure sensor array 160 and/or the signal conditioning module 164, and to generate an analysis of the set of signals in order to guide patient placement at the patient interface system 100. The processor 170 can thus comprise a first module 171 configured to receive the set of signals from the pressure sensor array 160, and a second module 172 configured to generate an analysis from the set of signals. In a first example, the analysis can confirm a uniform pressure distribution resulting from the patient's weight at the patient interface system 100. In a second example, the analysis can confirm a desired non-uniform pressure distribution resulting from the patient's weight at the patient interface system 100. In another example, the analysis can confirm an undesired uniform pressure distribution and/or an undesired non-uniform pressure distribution resulting from the patient's weight at the patient interface system 100. A uniform pressure distribution and/or a non-uniform pressure distribution confirmed by the analysis can then be used to guide or adjust the patient's configuration (e.g., torso position, body wall position, etc.) in order to facilitate scanning.

In some variations, guidance can be provided, as facilitated by the analysis generated by the processor 170, using visual and/or audio means for transmitting information. In one example, the analysis can be used to generate a rendering at a user interface 185 including a display configured to depict a current position of the patient, and a desired position of the patient that will produce a more desired pressure distribution. In another example, the analysis can be used to provide audio or text-based instructions to the patient and/or an operator (e.g., using a visual display, using a speaker), wherein the instructions facilitate adjustment of the patient's configuration relative to the patient interface system 100. In another example, the instructions can provide suggested system 100 configurations including one or more of: tilt angles of the planar portion 112 and/or the frustoconical portion 120 of the base 110, expanded and/or contracted configurations of the base 110, appropriate membrane sizes, appropriate membrane aperture sizes, appropriate tensioning ring 146 and/or spacer 148 thicknesses to achieve a desired tension across the membrane 150, and any other suitable configuration of any element of the system 100. Furthermore, in some variations of the example, the instructions can be provided to a controller 178 configured to automatically adjust system element configurations (e.g., tilt angles of the planar portion 112 and/or the frustoconical portion 120 of the base 110, expanded and/or contracted configurations of the base 110, appropriate membrane sizes, appropriate membrane aperture sizes, appropriate tensioning ring 146 and/or spacer 148 thicknesses, etc.) using an actuation subsystem 179 configured to manipulate a configuration of at least one element of the system 100.

As shown in FIG. 1, the system 100 can additionally include a retaining module 180, which functions to retain the patient in a desired configuration once the patient has been properly positioned relative to the patient interface system 100. The retaining module 180 can directly retain the patient's torso in a specific configuration, or can additionally or alternatively retain one or more of the patient's limbs/extremities to constrain patient motion. In some variations, the retaining module 180 can additionally or alternatively retain the patient's head/neck in a specific configuration to further limit patient movement. As such, the retaining module 180 can include one or more of: a belt, a strap, a cuff, a band, and any other suitable retaining element. The retaining module 180 preferably includes adjustable elements (e.g., adjustable straps, elastic bands, etc.) configured to provide an amount of restraint that constricts motion of the patient while still allowing patient comfort. The retaining element(s) can be coupled to the base no, the support assembly 130, the table topper 116, and/or any other suitable portion of the system 100 in a manner that retains a configuration of the patient relative to the system 100.

Preferred embodiments of the preferred patient interface system 100 include every combination of the base 110, the support assembly 130, the processor 170, the controller 178, the actuation subsystem 179, and the restraining module 180, and their respective components, including the planar portion 112 and the frustoconical portion 120 of the base 110, the table topper 116, frame 140, the membrane 150, the tensioning ring 146, the spacer 148, the pressure sensor array 160, and the conditioning module 164 of the support assembly 130. Furthermore, the system 100 can omit any one or more of the above described elements. For example, variations of the system 100 can omit the pressure sensor array 160, and can additionally or alternatively omit the tensioning ring(s) 146, the spacer(s) 148, and any other element configured to facilitate tensioning of the membrane 150.

2. Exemplary Use

In an exemplary use of an embodiment of the patient interface system, the patient interface system positions the breast of a patient to be scanned for ultrasound tomography. This example implementation is for illustrative purposes only, and should not be construed as definitive or limiting in scope of the claimed invention. In this example, a system operator or other translates various measurements of the patient into a selection of a suitable support assembly to be coupled to the base. These measurements can include any one or more of: breast size, patient weight, patient height, torso width, torso length, and any other suitable measurement, and correspond to a support assembly with at least a particular size of membrane aperture, and possibly to a particular set of adjustments to the base. The patient lies prone, stomach-side down, on the cushion of the base, and is positioned such that the breast to be scanned extends through the membrane aperture (and the aligned one or more apertures associated with the base) and into an imaging tank filled with water and an ultrasound transducer. Data generated from a pressure sensor array embedded in a flexible sheet coupled to the membrane and analyzed by a processor can be used to confirm proper positioning of the patient, and/or can be used to reposition the patient relative to the patient interface system, in order to improve data quality captured using the ultrasound transducer. The processor can generate a rendering that is displayed at a user interface accessible to at least one of the patient and the system operator, in order to guide positioning and/or repositioning of the patient at the patient interface system. The ultrasound transducer can then be activated to scan the breast tissue while the patient interfaces with the patient interface system, and acoustic data from the transducer can be analyzed by the processor and/or any suitable other processor to generate renderings of the breast based on one or more acousto-mechanical parameters including: acoustic reflection, acoustic attenuation, acoustic speed, and combinations thereof.

As a person skilled in the art will recognize from the previous detailed description and from the figures and claims, modifications and changes can be made to the preferred embodiments of the invention without departing from the scope of this invention defined in the following claims.

We claim:

1. A patient support system comprising:
   a base including a planar portion configured to support a patient in a prone configuration, and a frustoconical portion extending from a plane defined by the planar portion and defining a base aperture configured to receive a volume of tissue of the patient, the frustoconical portion comprising an inner sloped surface;
   a support assembly configured to couple to the base and support the volume of tissue, including a frame configured to abut to a top of the frustoconical portion of the base and a membrane retained within the frame, wherein the membrane defines a membrane aperture configured to align with the base aperture, and wherein the membrane is configured to deflect into the inner sloped surface of the frustoconical portion of the base while being retained in tension within the frame in response to a weight of the volume of tissue; and a pressure sensor array disposed proximal to at least one of the membrane and the frame, and configured to generate a set of signals in response to a distribution of the weight of the volume of tissue at the support assembly.

2. The system of claim 1, wherein at least a portion of the frustoconical portion of the base is configured to be seated within a recessed cavity on a shelf of the planar portion of the base.

3. The system of claim 2, wherein the frame includes a frame base, a bezel configured to abut a superior surface of the frame base, thereby forming a gap configured to receive the membrane, and a tensioning ring disposed at a radially inner surface of the bezel, wherein a peripheral portion of the membrane is configured to be retained within the gap, and wherein the membrane is further configured to be retained at the radially inner surface of the bezel by the tensioning ring, in order to maintain tension across the membrane.

4. The system of claim 3, further comprising a spacer configured to displace the tensioning ring from the frame base, thereby adjusting tension across the surface of the membrane.

5. The system of claim 1, wherein the pressure sensor array includes a set of sensors, uniformly distributed in a radial configuration within a flexible sheet in communication with at least one of the membrane and the frame.

6. The system of claim 1 further including
a processor configured to generate an analysis derived from the signals generated by the pressure sensor array, wherein the analysis is configured to facilitate positioning of the patient at the support assembly to achieve a desired patient configuration.

7. The system of claim 6, wherein the processor is further configured to provide instructions, configured to guide positioning of the patient, at a user interface for at least one of the patient and an operator of the system, based upon the analysis.

8. The system of claim 6, further comprising a controller configured to automatically adjust a configuration of at least one of the base and the support assembly in response to the analysis, thereby achieving the desired patient configuration.

9. A system comprising:
the patient support system of claim 1, and
a ring-shaped transducer array positioned proximal the base aperture, said ring-shaped transducer array comprising a set of ultrasound emitters configured to emit acoustic waveforms toward the volume of tissue, and a set of ultrasound receivers configured to generate a set of acoustic data based upon acoustic waveforms received from the volume of tissue.

10. The system of claim 1, wherein the membrane comprises a flexible polymer.

11. A patient support system comprising:
a base including a planar portion configured to support a patient in a prone configuration, and a frustoconical portion extending from a plane defined by the planar portion and defining a base aperture configured to receive a volume of tissue of the patient; and
a support assembly configured to couple to the base and support the volume of tissue, including a frame base defining a superior surface and an inferior surface configured to abut to a top of the frustoconical portion of the base, a bezel configured to couple to the superior surface of the frame base and provide a gap between the superior surface of the frame base and the bezel, and a membrane retained within the gap at a peripheral portion of the membrane, wherein the membrane defines a membrane aperture configured to align with the base aperture, and wherein the membrane is configured to deflect into the frustoconical portion of the base while being retained in tension within the gap in response to a weight of the volume of tissue.

12. The system of claim 11, wherein the base defines an obround surface, wherein the frustoconical portion is biased toward an end of a long axis of the base, and wherein the long axis of the base defines an axis of symmetry for the frustoconical portion.

13. The system of claim 12, wherein the membrane comprises a flexible polymer.

14. The system of claim 11, wherein at least a portion of the frustoconical portion of the base is configured to be seated within a recessed cavity on a shelf of the planar portion of the base.

15. The system of claim 11, wherein the base includes a head portion divided from a foot portion at an axis, and wherein the head portion is configured to be linearly displaced from the foot portion, and wherein the head portion is configured to be angularly displaced from the foot portion about the axis to produce a tilted configuration of the base.

16. The system of claim 11, wherein the system further includes a table topper, including an encased pliable material, disposed upon the planar portion of the base.

17. The system of claim 11, wherein the frame base of the support assembly is configured to couple to at least one membrane of a set of membranes, wherein the set of membranes includes the membrane, and wherein each membrane in the set of membranes defines a membrane aperture different in size from every other membrane aperture in the set of membrane apertures.

18. The system of claim 11, further comprising a tensioning ring disposed at a radially inner surface of the bezel, wherein the peripheral portion of the membrane is configured to be retained within the gap by a set of couplers configured to bias the bezel toward the frame base, and wherein the membrane is further configured to be retained at the radially inner surface of the bezel by the tensioning ring, in order to maintain tension across the membrane.

19. The system of claim 18, further comprising a spacer configured to displace the tensioning ring from the frame base, thereby adjusting tension across the surface of the membrane.

20. The system of claim 18, wherein the frame base is an annular frame base and is configured to be seated within an annular recess formed circumferentially between the frustoconical portion and the planar portion of the base, wherein the frustoconical portion of the base defines two perpendicular surfaces of the annular recess.

21. The system of claim 11, further including a pressure sensor array disposed proximal to a patient contact portion of the support assembly, wherein the pressure sensor array includes a set of pressure sensors configured to generate signals in response to a distribution of the patient's weight at least at one of the membrane and the frame base.

22. The system of claim 21, further including a processor configured to generate an analysis derived from the signals generated by the pressure sensor array, wherein the analysis is configured to facilitate positioning of the patient at the support assembly to achieve a desired patient configuration.

* * * * *

UNITED STATES PATENT AND TRADEMARK OFFICE
CERTIFICATE OF CORRECTION

PATENT NO. : 10,123,770 B2  
APPLICATION NO. : 14/208181  
DATED : November 13, 2018  
INVENTOR(S) : James Szpak et al.

Page 1 of 1

It is certified that error appears in the above-identified patent and that said Letters Patent is hereby corrected as shown below:

On the Title Page

(72) Inventors: Column 1, Line 4:
"Roman Janeer, Plymouth, MI"
Should read:
-- Roman Janer, Plymouth, MI --

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*